US011933892B2

(12) United States Patent
Fish et al.

(10) Patent No.: US 11,933,892 B2
(45) Date of Patent: Mar. 19, 2024

(54) ULTRASOUND IMAGING SYSTEM AND METHOD

(71) Applicant: KONINKLIJKE PHILIPS N.V., Eindhoven (NL)

(72) Inventors: David Andrew Fish, Worthing (GB); Gerardus Johannus Jacobus Maria Arnoldussen, Eindhoven (NL); Sotir Filipov Ouzounov, Eindhoven (NL); Emil Dimitrov Totev, Delft (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1058 days.

(21) Appl. No.: 16/074,126

(22) PCT Filed: Jan. 20, 2017

(86) PCT No.: PCT/EP2017/051128
§ 371 (c)(1),
(2) Date: Jul. 31, 2018

(87) PCT Pub. No.: WO2017/133900
PCT Pub. Date: Aug. 10, 2017

(65) Prior Publication Data
US 2021/0124042 A1 Apr. 29, 2021

(30) Foreign Application Priority Data
Feb. 4, 2016 (EP) .................... 16154161

(51) Int. Cl.
G01S 15/89 (2006.01)
A61B 8/06 (2006.01)
(Continued)

(52) U.S. Cl.
CPC ........ G01S 15/8927 (2013.01); B06B 1/0207 (2013.01); G01S 7/52025 (2013.01);
(Continued)

(58) Field of Classification Search
None
See application file for complete search history.

(56) References Cited

U.S. PATENT DOCUMENTS 4,345,251 A * 8/1982 Begeman ............... H04Q 3/521
340/2.26
5,997,479 A 12/1999 Savord et al.
(Continued)

FOREIGN PATENT DOCUMENTS

CN 102138807 A * 8/2011 ............... A61B 8/00
JP 2010142639 A 7/2010
(Continued)

OTHER PUBLICATIONS

Bose, Soumya, and Pradip Mandal. "A fully differential amplifier with CMOS feedback biasing for sensing CMUT signals." Proceedings of the 2014 IEEE Students' Technology Symposium. IEEE, 2014. (Year: 2014).*
(Continued)

Primary Examiner — Isam A Alsomiri
Assistant Examiner — Jonathan D Armstrong

(57) ABSTRACT

An ultrasound imaging system has an array of ultrasound transducers comprising a set of sub-arrays of transducers. Each transducer (100) has an analogue buffer (106). Each sub-array of transducers has a signal path (102, 104) from within the array of ultrasound transducers to outside the array of ultrasound transducers which comprises one or more hops between the buffers (106). To reduce the signal line length from inside the array of ultrasound transducers to the periphery, at least some multiple hops between buffers (106) are provided. Each buffer hop introduces a delay, but prevents signal degradation so that a large number of analog signals can be transmitted across the large area ASIC of the transducer array.

15 Claims, 11 Drawing Sheets

(51) Int. Cl.
*A61B 8/08* (2006.01)
*B06B 1/02* (2006.01)
*G01S 7/52* (2006.01)

(52) U.S. Cl.
CPC ............... *G01S 7/5208* (2013.01); *A61B 8/06* (2013.01); *A61B 8/0825* (2013.01); *A61B 8/0883* (2013.01); *A61B 8/485* (2013.01); *B06B 2201/51* (2013.01); *B06B 2201/55* (2013.01); *B06B 2201/76* (2013.01)

(56) References Cited

U.S. PATENT DOCUMENTS

| | | | |
|---|---|---|---|
| 6,013,032 A | 1/2000 | Savord | |
| 6,283,919 B1 | 9/2001 | Roundhill et al. | |
| 6,443,896 B1 | 9/2002 | Detmer | |
| 6,458,083 B1 | 10/2002 | Jago et al. | |
| 6,530,885 B1 | 3/2003 | Entrekin et al. | |
| 6,623,432 B2 | 9/2003 | Powers et al. | |
| 7,800,979 B2 | 9/2010 | Hu et al. | |
| 8,176,787 B2 | 5/2012 | Haider et al. | |
| 9,171,859 B2* | 10/2015 | Oh | H01L 27/11578 |
| 9,229,097 B2* | 1/2016 | Rothberg | G01S 7/52019 |
| 9,327,142 B2* | 5/2016 | Rothberg | G01S 15/8915 |
| 9,351,706 B2* | 5/2016 | Rothberg | A61B 8/4477 |
| 9,592,032 B2* | 3/2017 | Rothberg | A61B 8/4483 |
| 9,739,875 B2 | 8/2017 | Koptenko | |
| 10,107,901 B2* | 10/2018 | Guenther | G01S 7/52053 |
| 2006/0008168 A1 | 1/2006 | Lee | H04N 19/46 |
| | | | 382/250 |
| 2006/0010358 A1* | 1/2006 | Miller | G01R 31/3016 |
| | | | 714/700 |
| 2008/0114240 A1 | 5/2008 | Sasaki | |
| 2009/0016163 A1* | 1/2009 | Freeman | G01S 15/8909 |
| | | | 367/103 |
| 2009/0095722 A1* | 4/2009 | Ehrmann | B23K 26/0648 |
| | | | 219/121.72 |
| 2009/0121973 A1* | 5/2009 | Kim | G09G 3/3266 |
| | | | 345/55 |
| 2009/0171213 A1* | 7/2009 | Savord | G01S 7/5208 |
| | | | 600/447 |
| 2010/0020645 A1* | 1/2010 | Wodnicki | G01S 15/8927 |
| | | | 367/155 |
| 2010/0152587 A1 | 6/2010 | Haider et al. | |
| 2011/0021923 A1* | 1/2011 | Daft | G01S 15/8925 |
| | | | 600/459 |
| 2011/0172537 A1 | 7/2011 | Hongou et al. | |
| 2011/0295119 A1* | 12/2011 | Miller | G01S 15/8925 |
| | | | 600/443 |
| 2013/0310679 A1* | 11/2013 | Natarajan | A61B 8/466 |
| | | | 600/411 |
| 2014/0056099 A1* | 2/2014 | Hancock | A61B 8/445 |
| | | | 367/11 |
| 2014/0164629 A1* | 6/2014 | Barth | H04L 67/141 |
| | | | 709/227 |
| 2015/0071031 A1 | 3/2015 | Siedenburg et al. | |
| 2015/0087991 A1 | 3/2015 | Chen et al. | |
| 2015/0206895 A1* | 7/2015 | Oh | H01L 29/7926 |
| | | | 257/324 |
| 2015/0297193 A1* | 10/2015 | Rothberg | A61B 8/4483 |
| | | | 600/459 |
| 2015/0301165 A1* | 10/2015 | Rothberg | B06B 1/0607 |
| | | | 367/117 |
| 2016/0249882 A1* | 9/2016 | Degertekin | A61B 1/05 |
| | | | 600/424 |
| 2017/0330553 A1* | 11/2017 | Garlepp | G10K 11/346 |
| 2018/0064418 A1* | 3/2018 | Savord | G01S 15/8925 |
| 2018/0064419 A1* | 3/2018 | Savord | G10K 11/341 |
| 2018/0317889 A1* | 11/2018 | Carpenter | G01S 7/5208 |
| 2019/0142387 A1* | 5/2019 | Chen | A61B 8/54 |
| | | | 367/135 |
| 2019/0196012 A1* | 6/2019 | Savord | G01S 7/52095 |
| 2019/0212424 A1* | 7/2019 | Savord | A61B 8/56 |
| 2020/0279087 A1* | 9/2020 | Seo | G01S 7/5202 |
| 2021/0069749 A1* | 3/2021 | Durocher | B06B 1/0685 |

FOREIGN PATENT DOCUMENTS

| | | |
|---|---|---|
| JP | 2011142931 A | 7/2011 |
| KR | 20120096736 A | 8/2012 |

OTHER PUBLICATIONS

David F Lemmerhirt et al: "A 32 × 32 capacitive micromachined ultrasonic transducer array manufactured in standard CMOS", IEEE Transactions on Ultrasonics, Ferroelectrics and Frequency Control, vol. 59, No. 7, Jul. 1, 2012 (Jul. 1, 2012), pp. 1521-1536.

Wygant et al: "Integration of 2D CMUT arrays with front-end electronics for volumetric ultrasound imaging", IEEE Transactions on Ultrasonics, Ferroelectrics and Frequency Control, vol. 55, No. 2, Feb. 1, 2008 (Feb. 1, 2008), pp. 327-342.

* cited by examiner

ULTRASOUND IMAGING SYSTEM AND METHOD

This application is the U.S. National Phase application under 35 U.S.C. § 371 of International Application No. PCT/EP2017/051128 filed on Jan. 20, 2017, which claims the benefit of EP Application Serial No. 16154161.0, filed Feb. 4, 2016. These applications are hereby incorporated by reference herein.

FIELD OF THE INVENTION

This invention relates to ultrasound imaging systems, and in particular having a large area array of ultrasound sensors.

BACKGROUND OF THE INVENTION

Large area ultrasound is proposed as a method to enable reproducible, fast, high quality imagery and ease of use based on a reduced need for specialist sonographers. Such systems may also be designed to find optimal operating conditions automatically. They are large area so that they can cover large areas of the body which therefore enables views from the best angles to be searched for and used in an automated manner which is repeatable.

Ultrasound probes are typically implemented as an ultrasound transducer coupled to a CMOS ASIC. The ultrasound transducer can also be implemented as part of the CMOS process, as is the case for capacitive micromachined ultrasonic transducer (CMUT) devices. Large area ultrasound probes can be constructed from a single large piece of silicon or can be constructed from the tiling of multiple individual tiles of probes.

FIG. 1 shows a large area ultrasound system in the form of a ASIC having an array of, for example 800×800, transducers each of size 250 µm×250 µm giving a 20 cm×20 cm ASIC. The dynamic aperture of the array (i.e. the set of transducers which is read out simultaneously at any given point in time) is a smaller array, for example a 50×50 sub-array 1 of transducers. To read out this set of elements, 2500 analog to digital converters (ADCs) are provided, shown as region 2 outside (periphery) the transducer array. There are also 100 low voltage differential signal transmitters shown as region 4.

Instead of an array of probes on a common silicon substrate, and array of separate probes may be provided as shown in FIG. 2. There are individual probes 6 spaced by gaps 8 as shown in the plan view. As shown in the two side views, this enables curvature to be introduced to fit to the human body.

A problem with this type of system is how to take data from the large area ASIC system, which is very much larger than current commercially available systems, at a sufficient speed to enable rapid ultrasound imaging.

Even though the large area system has many more individual probes, only a small portion of them will be on at any given time. As mentioned above, ultrasound apertures of the order of 50×50 elements may be appropriate even though the whole system may have 256 times as many elements i.e. 800×800 as in the example above.

When the ASIC is very large, the imaging time also becomes large, for example too large for breast screening and monitoring. In current systems, a scanning time of 30 minutes per breast is typical. Therefore faster imaging is desirable. Also, certain imaging modes have a much higher speed requirement e.g. elastography and vector flow imaging.

Therefore, to provide the capability of a fast examination in breast imaging, there is a need for an increase in imaging speed of two orders of magnitude. Imaging modes such as vector flow and elastography require even greater speed improvements, for example above 1000 Hz operation.

These desired speed increases pose particular problems for the transport of signals from the ultrasound probe array. Some very basic assumptions about the imaging can be made, such as an ultrasound wavelength of 0.5 mm, an aperture of 1.25 cm, with a resolution in angle of about 1 degree. In this case, an imaging procedure covering+/−30 degrees equates to 60 scans.

Assuming a 10 cm depth is required with a speed of sound of 1500 m/s then the transmit-receive time is 134 µs, so of the order of 200 µs. For 3D imaging, scans are needed under two orthogonal angles so the required scan time becomes 60×60×0.0002=0.72 seconds.

If the large area system has 800×800 elements and the aperture is 50×50 transducers as in the example above, then to scan across the whole system in steps of 50 elements in the x and y directions across the array gives 16×16=256 steps. Therefore the overall imaging time becomes 3.1 minutes.

If 3D imaging is not required, a 1D system may be scanned across the 2D array. Taking the same parameters as above with a 20 cm×20 cm large area array and element pitch of 250 µm then 800 1D scans takes 60*800*0.0002=9.6 seconds in one direction (x-axis). To cover the y-axis direction this needs several repeats e.g. 20 cm/1.25 cm=16, so overall time would be 9.6×16=153.6 seconds i.e. 2.6 minutes.

Other imaging modes could make this time even longer. Given that these times are much greater than the breathing or movement time, there are likely to be imaging artifacts even when the organ to be imaged is relatively still. If the heart or blood flow imaging is considered (3D vector flow) then the situation is more acute. Therefore there is a need for ultrafast imaging in the large area context.

Ultrafast imaging can use plane or diverging wave transmits and uses coherent compounding to construct an image over for example 20 transmits. If all points in the image can be received at once, the above time period of 60×60×0.0002=0.72 seconds can be shortened to 20×0.0002=4 ms. The overall imaging time then becomes 1.6 seconds. Therefore movement are breathing will be more easily accommodated. In the case of a fast moving organ e.g. the heart, the aperture may be required in only a small number of positions to reduce the overall time.

One standard ASIC approach is to perform analog micro beamforming of a number of elements in a patch, to reduce the number of analog outputs. For example, analog beam forming could be applied to patches within the 50×50 aperture discussed above. Each patch can be quite a large number of elements e.g. 8×9=72. For example, a smaller complete ASIC may have 9216 elements. Standard ultrasound systems are often limited to 128 analogue outputs, therefore they perform analogue beamforming on the ASIC by grouping elements into rectangular patches of this 72 element size (72*128=9216). Of course, these figures are simply by way of example. Digital beamforming is then performed off chip in the ultrasound system which has 128 ADCs. By reducing the number of output channels to 128 in this way, analogue signals at frequencies up to 40 Mhz can be read readout in an analogue manner from the probe ASIC.

However, if ultrafast imaging is required, using plane wave coherent compounding, micro beamforming over large patches becomes error prone and the image quality is compromised. This becomes especially acute in the near field where angles are much larger. Therefore micro beamforming is less useful particularly at large patch sizes. Micro beamforming with small patch sizes such as 2×2 (625 channels for a 50×50 aperture) or 3×3 (278 channels for a 50×50 aperture) may be preferred.

In FIG. 1, the ADC blocks 2 are shown on the same ASIC as the array of transducers. However, this need not be the case. The main problem is getting the large number of signals from the ultrasound aperture to the ADC block 2 if it is on the ASIC or to analogue line drivers to transport the data off of the ASIC if the ADC block is external to the ASIC. In such a large ASIC, the line loads will be very large.

By way of example, a typical 0.18 µm CMOS technology which uses reticule stitching may have line widths for metal tracking which will be quite large e.g. 1 µm with a line pitch of 2 µm. Assuming all 2500 elements need to be read out, 2×50 differential wires will occupy 200 µm of space.

If the individual element size is 250 µm, then with a CMOS process with a high metal stack this should be no issue. If 50 elements of data need to be readout in the space of one column of elements, this means the 2500 elements of data can be readout within the width of 50 elements. Therefore wherever the aperture is within the ASIC the data can be tracked to the edge of the ASIC in a simple manner.

Considering the line loads, some typical values for a 0.18 µm CMOS 6 metal process are (where metal 1 is closest to the substrate):

Example Metal Widths and Resistances

| Metals 1 to 4 | 0.1 Ohms/Sq |
| Metal 5 | 0.05 Ohms/Sq |
| Metal 6 | 0.01 Ohms/Sq |

Example Parasitic Capacitances

| Metal to Metal | 100 aF/µm |
| Metal to lower metal | 50 aF/µm$^2$ |

A metal with the characteristics of Metal 5 above is suitable for the large area scenario. A top metal will be required for supply and will be very wide e.g. minimum width of 3 µm. The metals 1 to 4 could also be used but the resistance is rather high.

A calculation of the parasitic capacitance and resistance of a wire tracking across a 20 cm ASIC reveals the following:

Parasitic Capacitance

The capacitance across 20 cm of one wire might be estimated as: 200 aF/µm*200000 µm+100 aF/µm$^2$*1 µm*200000 µm=40 pF+20 pF=60 pF.

Assuming one switch per transducer, which will need to have a low on-resistance, a gate/source/drain capacitance of 50 fF may be assumed. There will be 800 vertically across the array so that the capacitance from the transistors would be 40 pF. Therefore the total vertical track capacitance is of the order of 100 pF. This doubles if horizontal tracks are also used.

Parasitic Resistance

The vertical wire resistance is of the order of 0.05 Ohms/sq*200000 sq=10K Ohms. Again, this doubles if horizontal tracks are also used.

This means the vertical line time constant ($\tau$=RC) will be of the order of 1 µs. To charge to 10 bit accuracy will require about 7 time constants. Therefore it will not be possible to transmit analogue signals this distance on an ASIC of size 20 cm at 40 MHz sample rate. Even taking into account superior technology variations, this analogue data transfer rate is not possible.

This analysis shows that one fundamental problem is how to retrieve data from the large ultrasound array to the edge of the ASIC for data conversion or transfer, particularly when there are a large number of analogue signals to move across the ASIC.

In a tiled system such as shown in FIG. 2, the issues become even more difficult due to the parasitic capacitance of bond-pads between the tile ASICs which can be of the order of 10 pF.

SUMMARY OF THE INVENTION

The invention is defined by the claims.

According to examples in accordance with an aspect of the invention, there is provided an ultrasound imaging system, comprising:

an array of ultrasound transducers comprising a set of sub-arrays of transducers; and an array of analogue buffers, with an analog buffer associated with each transducer, and located locally at the location of the respective transducer, wherein each sub-array of transducers has a set of signal paths, with one signal path for each transducer, from within the array of ultrasound transducers to outside the array of ultrasound transducers which for at least some of the transducers comprises multiple hops between the analogue buffers.

This system incorporates buffers into the array of transducers. To reduce the signal line length, multiple hops between buffers are provided (although for a transducer at the very periphery of the array, multiple hops may not be needed). Each buffer hop introduces a delay, but prevents signal degradation by reducing the signal line time constant, in particular by reducing the maximum signal line length over which the signal travels, and therefore reducing the resistance and capacitance. In this way, a large number of analog signals can be transmitted across the large area ASIC of the transducer array. It is then possible to compensate for the any differences in delay since these are known in advance, so that beamforming can be achieved. The sub-array of transducers for example corresponds to the sensing aperture.

The system may comprise an array of banks of analog to digital converters, wherein each signal path leads to a respective bank or set of banks of analog to digital converters. Thus, the signal paths remain in the analog domain so that limited circuitry is needed.

In one arrangement, the array of ultrasound transducers is provided as an integrated circuit such as an ASIC and the array of banks of analog to digital converters is provided as part of the integrated circuit. This forms a complete integrated solution.

Alternatively, the banks of analog to digital converters may be provided on a separate substrate to the array of ultrasound transducers. The ultrasound transducers may themselves be formed as separate probes.

The hops may be evenly distributed along the signal path. In this way, the signal path distance between buffer operations is kept to a minimum (for a given number of hops).

Each buffer of each set of analog buffers may comprise a differential amplifier with unity gain or a sample and hold circuit.

In one arrangement, the array of ultrasound transducers comprises rows and columns of ultrasound transducers, and the signal paths form columns. In this way, the signal paths extend in lines to the periphery of the array of ultrasound transducers. The number of hops may be a function of the distance of the respective ultrasound transducer from the periphery.

A second array of analog buffers may then be located in rows outside the area of the array of ultrasound transducers. These may be used to distribute one signal path line along the periphery so that a distributed arrangement of analog to digital converters may be used.

In another arrangement, a second array of analog buffers is located within the area of the array of ultrasound transducers such that signal paths within the array of ultrasound transducers form zig-zag paths. In this case, the signal paths do not extend directly to the periphery but may follow a more complex route, with row direction and column direction components.

In another arrangement each transducer may comprise a circuit which comprises:
    the analog buffer;
    a switching arrangement; and
    a register for controlling the switching arrangement,
    wherein the switching arrangement is selectively configurable to route the transducer output to a selected output of the circuit or to route an external input to the circuit to an external output from the circuit through the buffer.

This circuit is configurable to provide a buffer function or a transducer output function. In this way, the hop pattern can be set by updating the register control. The routing through the buffer may be in line, for example with a row direction input and a row direction output, or with a column direction input and a column direction output. However, it may also enable a 90 degree or 180 degree redirection.

The signal paths for example have the same number of hops for each transducer. In this way, each signal path experiences the same delay. This is particularly suitable for buffers in the form of sample and hold circuits, since they impose a clocking delay. The equal signal path length may be achieved within the array of transducers, or after including a portion outside the array of transducers. The final signal path locations may again be distributed along the periphery so that a distributed arrangement of analog to digital converters may be used.

If there are instead different numbers of hops in different signal paths (and of particular interest when a sample and hold circuit is used as the buffer), the system may further comprise:
    a memory for storing information concerning a delay associated with each transducer;
    a processor for processing the transducer signals, taking into account the delays stored in the memory.

This enables the data processing to take account of the signal paths. The signal path length is then a function of the distance of a transducer to the periphery, and it enables the path lengths to be kept as short as possible with as few hops as possible.

Examples in accordance with another aspect of the invention provide an ultrasound imaging method, comprising:
    generating ultrasound signals using an array of ultrasound transducers comprising a set of sub-arrays of transducers;
    buffering the outputs from each transducer using an associated analogue buffer located locally at the location of the respective transducer; and
    for each sub-array of transducers, forming a signal path for each transducer of the sub-array from within the array to outside the array which for at least some of the transducers comprises multiple hops between the analogue buffers.

Each signal path may lead to a respective bank or set of banks of analog to digital converters. The hops may be spread evenly along a path from each transducer to outside the array.

The array of ultrasound transducers may comprise rows and columns of ultrasound transducers, and wherein the method comprises forming signal paths as columns to reach the edge of the area of the array of ultrasound transducers, and providing further signal paths between analog buffers of a second array located in rows outside the area of the array of ultrasound transducers. Alternatively, the signal paths may include a second array of analog buffers located within the area of the array of ultrasound transducers, wherein the method comprises forming zig-zag signal paths within the array of ultrasound transducers.

In either case, signal paths may be formed with the same number of hops for each transducer.

Alternatively, information may be stored concerning a delay associated with each transducer and the method then comprises processing the transducer signals, taking into account the stored delays. Different signal paths for different transducers may then have different numbers of hops, and the path lengths may be kept as short as possible.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides an ultrasound imaging system which has an array of ultrasound transducers comprising a set of sub-arrays of transducers. Each transducer has a local analogue buffer. Each sub-array of transducers has a set of signal paths from within the array of ultrasound transducers to outside the array of ultrasound transducers which each comprise one or more hops between the analogue buffers. To reduce the signal line length from inside the array of ultrasound transducers to the periphery, at least some multiple hops between buffers are provided. Each buffer hop introduces a delay, but prevents signal degradation so that a large number of analog signals can be transmitted across the large area ASIC of the transducer array.

Figure 3:
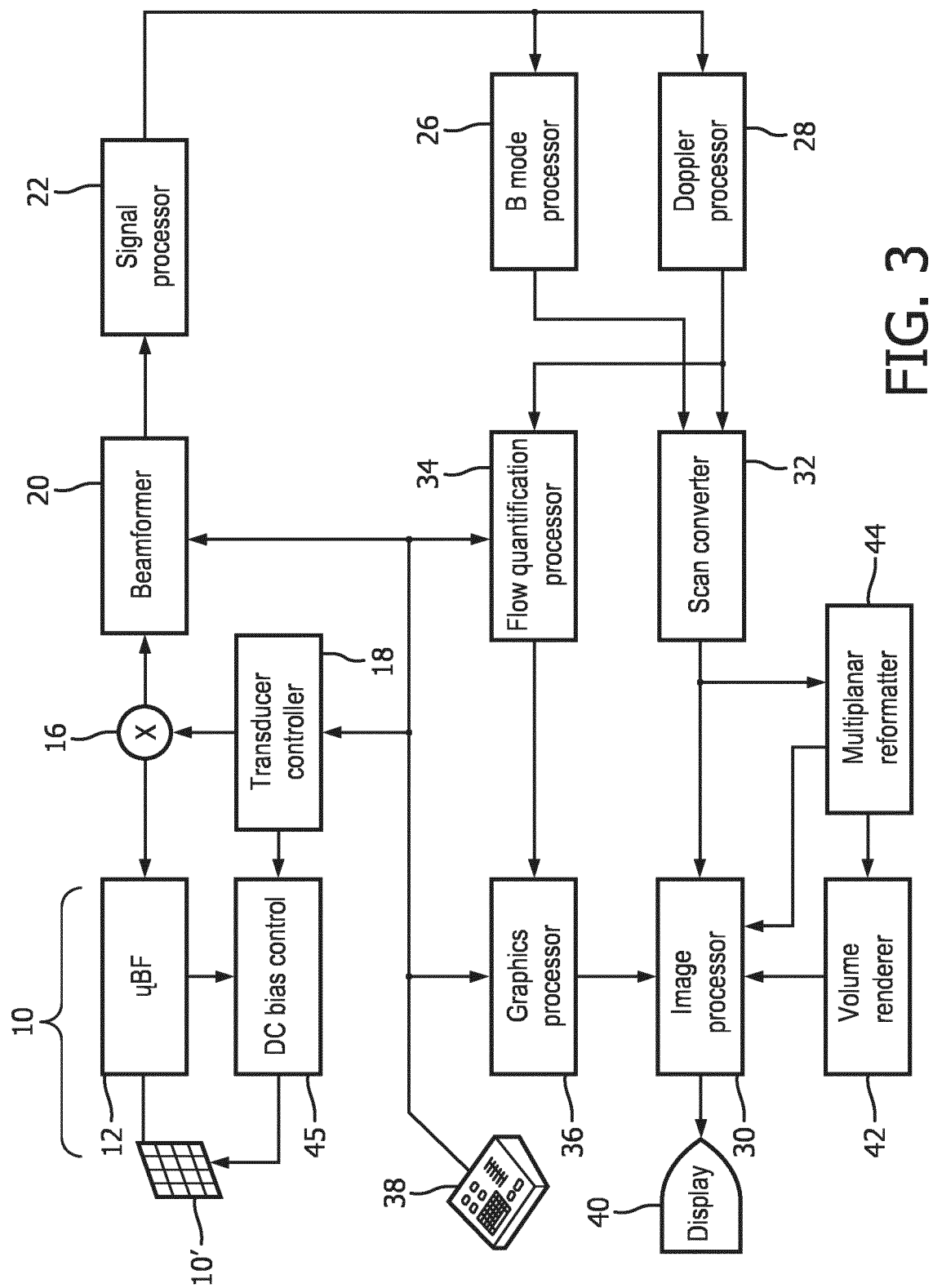
FIG. 3 shows an ultrasound diagnostic imaging system to explain the general operation.

The general operation of an ultrasound diagnostic imaging system will first be described, with reference to FIG. 3, and with emphasis on the reception function of the system since this invention relates to the routing of transducer signals from the transducer array.

The system comprises an array transducer probe 10 which has a CMUT transducer array 10' for transmitting ultrasound waves and receiving echo information. The transducer array 10' may alternatively comprise piezoelectric transducers formed of materials such as PZT or PVDF. The transducer array 10' is a two-dimensional array of transducers capable of scanning in a 2D plane or in three dimensions for 3D imaging.

The transducer array 10' is coupled to a microbeamformer 12 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 12 is coupled by the probe cable to a transmit/receive (T/R) switch 16 which switches between transmission and reception and protects the main beamformer 20 from high energy transmit signals when a microbeamformer is not used and the transducer array is operated directly by the main system beamformer. The transmission of ultrasound beams from the transducer array 10 is directed by a transducer controller 18 coupled to the microbeamformer by the T/R switch 16 and a main transmission beamformer (not shown), which receives input from the user's operation of the user interface or control panel 38.

One of the functions controlled by the transducer controller 18 is the direction in which beams are steered and focused. Beams may be steered straight ahead from (orthogonal to) the transducer array, or at different angles for a wider field of view. The transducer controller 18 can be coupled to control a DC bias control 45 for the CMUT array. The DC bias control 45 sets DC bias voltage(s) that are applied to the CMUT cells.

In the reception channel, partially beamformed signals are produced by the microbeamformer 12 and are coupled to a main receive beamformer 20 where the partially beamformed signals from individual patches of transducers are combined into a fully beamformed signal. For example, the main beamformer 20 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 22. The signal processor 22 can process the received echo signals in various ways, such as band-pass filtering, decimation, I and Q component separation, and harmonic signal separation which acts to separate linear and nonlinear signals so as to enable the identification of non-linear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

Figure 1:
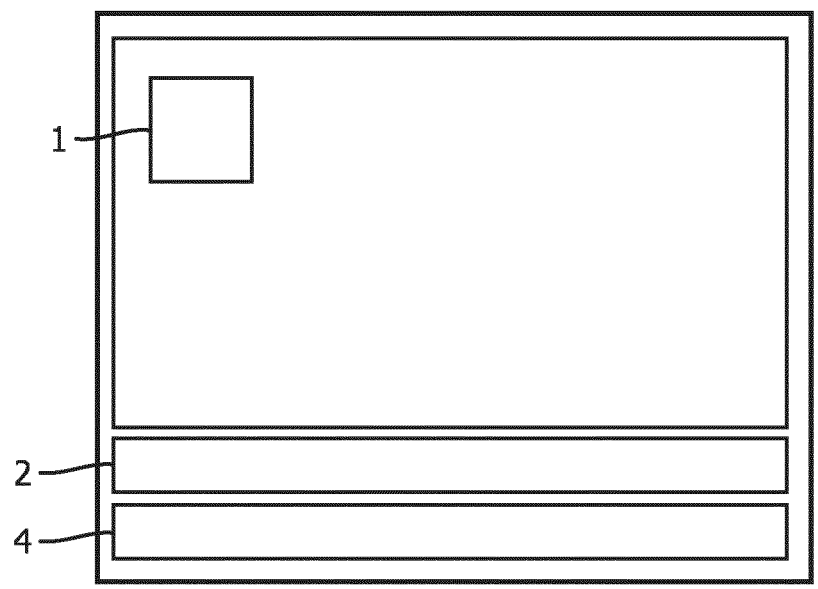
FIG. 1 shows a large area ultrasound system in the form of a ASIC having an array of transducers.

The beamformers for transmission and for reception are implemented in different hardware and can have different functions. Of course, the receiver beamformer is designed taking into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 10' which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 26 and a Doppler processor 28. The B mode processor 26 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor 28 typically includes a wall filter with parameters which may be set to pass and/or reject echoes returned from selected types of materials in the body.

For instance, the wall filter can be set to have a pass band characteristic which passes signals of relatively low amplitude from higher velocity materials while rejecting relatively strong signals from lower or zero velocity material. This pass band characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 32 and a multi-planar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made. Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 10' and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

This invention relates to the routing of received transducer signals form the elements of transducer array to the periphery of the array.

Figure 4:
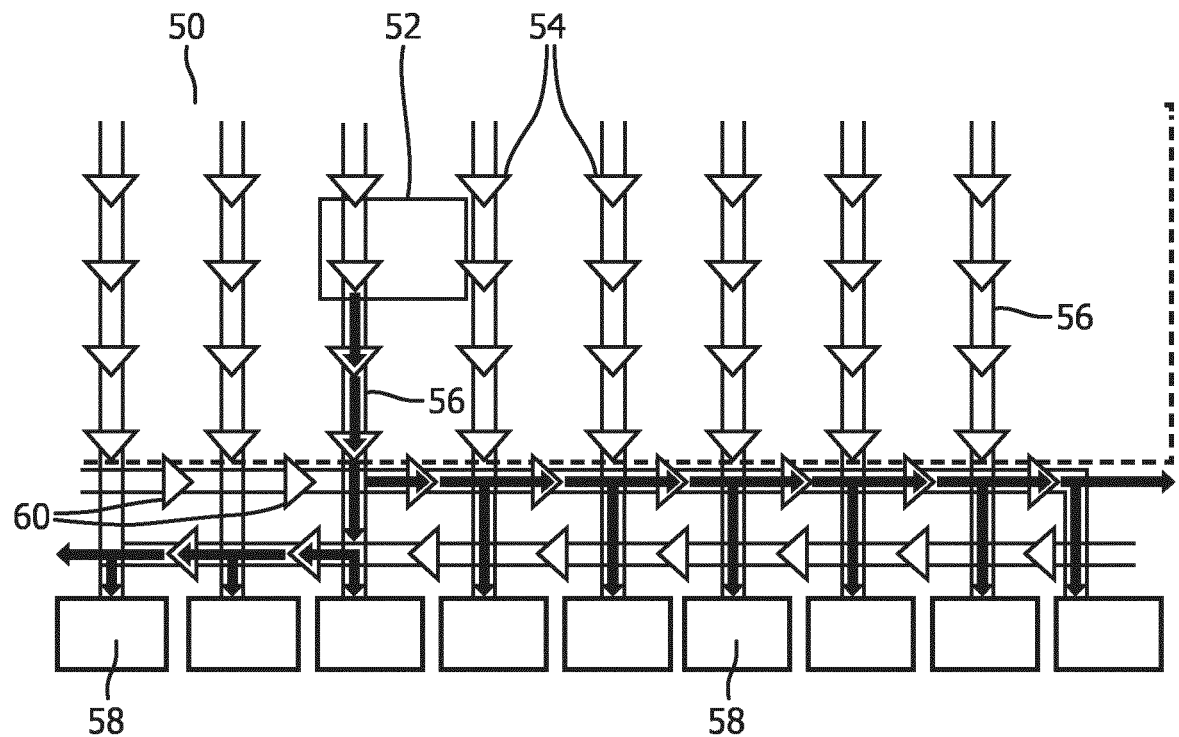
FIG. 4 shows a first example of ultrasound imaging system making use of the approach of the invention.

FIG. 4 shows a first example of ultrasound imaging system making use of the approach of the invention.

There is an area 50 which comprises the transducer array. The array comprises a set of sub-arrays 52 of transducers, arranged in rows and columns. Each sub-array comprises a plurality of transducers. For example, following the example given above, each sub-array 52 may comprise 50×50 individual transducers. Of course any other number of individual transducers in the sub-array is possible.

The transducer array is provided with an array of analog buffers. Each transducer sub-array 52 may thus be considered to be associated with a set 54 of analogue buffers. These are located at the location of the respective sub-array 52 of transducers. Note that the transducer array is a regular array of transducers. It can be thought of as a set of sub-arrays, since the signals only from a sub-array are processed at any one time. The sub-array being processed forms the imaging aperture and it may be moved around the array. It may be moved between non-overlapping positions, or the different positions at which the sub-array may be processed may overlap.

When the signals from one sub-array are being processed, the other transducers are off and in a high impedance state so that they do not couple to the signal paths.

In FIG. 4, each set 54 of analog buffers is shown as one unit. This is to represent the processing of all signals generated by the ultrasound probe aperture in a simple way. In reality, the individual buffers form a regular array, with each individual buffer located adjacent its own local transducer. Each set 54 of analogue buffers is generally located within (i.e. at) a respective transducer sub-array, and there is a one-to-one mapping between each buffer and a transducer, and thus also between each set 54 of buffers and a transducer sub-array. In this way, there is a short signal path from the transducer within the sub-array 52 to its local buffer within the set 54 of buffers. Each buffer may be a buffer circuit having multiple buffer elements. The local location of the buffer with associated to it transducer may be arranged, for example, either within the same plane as the transducer sub-array or in a circuitry layer above or below the plane of said transducer sub-array. In both cases the buffer is located in a vicinity of the associated transducer such that a short interconnection line can be realized.

Each sub-array 52 of transducers has a signal path 56 from within the array 50 of ultrasound transducers to outside the array 50 of ultrasound transducers. The signal path comprises one or more hops, and in practice multiple hops, between the buffers. In this example, the signal paths form columns. In this way, the signal paths extend in column lines to the periphery of the array 50 of ultrasound transducers.

To reduce the signal line length between buffer operations, multiple hops between buffers are provided.

The hops may be spaced evenly between buffers extending in series between a given transducer and the periphery. The signals from the different transducers may have the same number of hops to reach the periphery, but equally there may be a number of hops which is a function of the position of a given transducer within the array. The multiple hops are preferably made at uniform distances along the signal path. In this way, the signal path distance between buffer operations is kept to a minimum. There may be further buffers between those associated with the transducers.

By way of example, for the sub-array 52 shown, there are three sub-arrays of buffers before the signal path reaches the edge of the array 50. If each sub-array of buffers is a 50×50 array of buffers, then there are up to 150 buffer hops that can be made in the column direction alone. As explained below, around 40 buffer hops may be appropriate for the full signal column. Thus, the buffering does not take place at each adjacent buffer in a column, but takes place every n buffers in the column so that the required number of signal hops is made, or looked at differently, so that the maximum signal path length is determined.

Each buffer hop typically introduces a delay, but prevents signal degradation by reducing the analog signal transmission distance, and therefore the signal line resistance and capacitance, so that a large number of analog signals can be transmitted across the large area ASIC of the transducer array at high speed.

The signal paths eventually lead to an array of banks 58 of analog to digital converters. In the example of FIG. 4, the banks 58 of analog to digital converters extend along an axis of the area 50.

Again, the digital to analog converters are shown as banks simply for ease of representation. They simply form an array, and the array may be considered as a set of banks simply to provide notional partitioning corresponding to the partitioning of the array of transducers into sub-arrays.

There is a fixed mapping between each transducer and an associated analog to digital converter, so that for each possible ultrasound aperture, one transducer provides its signal to a dedicated one of the analog to digital converters. The signal path thus splits between all of the banks 58 of analog to digital converters. This assumes no analog microbeamforming (to reduce the number of analog to digital converters) but analog microbeamforming may additionally be employed.

This arrangement resolves the RC timing issue. However there will be variable delays between the ultrasound transducers at the aperture and the banks 58 of converters.

By having the analogue to digital converters grouped along one edge of the area 50 (which is the area of an ASIC) then horizontal signal paths are needed as well as vertical signal paths as the ADCs will be quite large. For these horizontal signal paths, a second array of analog buffers is located in rows outside the area of the array 50 of ultrasound transducers. These are shown grouped into sets 60 simply for ease of representation. These may be used to distribute one signal path line along the periphery so that a distributed arrangement of analog to digital converter banks 58 may be used.

The horizontal buffers 60 operate in both directions. The vertical buffers process signals from the sub-arrays 52 of transducers, and the buffers at the transducers could in principle be re-used for data transfer (i.e. performing the hops) if they are not actively used in the aperture, to transmit data from the transducers towards the converters.

The arrows forming the buffer symbols show the direction of data flow. As explained above, each set of buffers is in practice a bus of buffers corresponding in number to the number of transducers in the aperture (2500 for a 50×50 sub-array). Each bank 58 of analog to digital converters will in this example include 2500/16=156 analog to digital converters (there are 16 rows of sub-arrays 52 hence 16 column direction signal paths 36). Thus, 16 banks of 156 analog to digital converters are needed for this example.

Each signal path thus leads to the full set of banks 58 of analog to digital converters. Thus, within the 50×50 sub-array (which can be selected anywhere within the full ASIC). a first 156 transducers can be considered to be routed to the first bank of 156 ADCs, then the next 156 transducers are routed to the second bank of 156 ADCs and so on.

The bold paths in FIG. 4 show the way the signal path from one sub-array of transducers 52 reaches all 16 banks 58 of analog to digital converter (only 9 banks are shown for simplicity).

In FIG. 4, the banks 58 of analog to digital converters are provided separate to the substrate of the array 50 of ultrasound transducers. However, the array of ultrasound transducers may instead be provided as an integrated circuit such as an ASIC and the array of banks of analog to digital converters may be provided as part of the integrated circuit. This forms a complete integrated solution.

Figure 5:
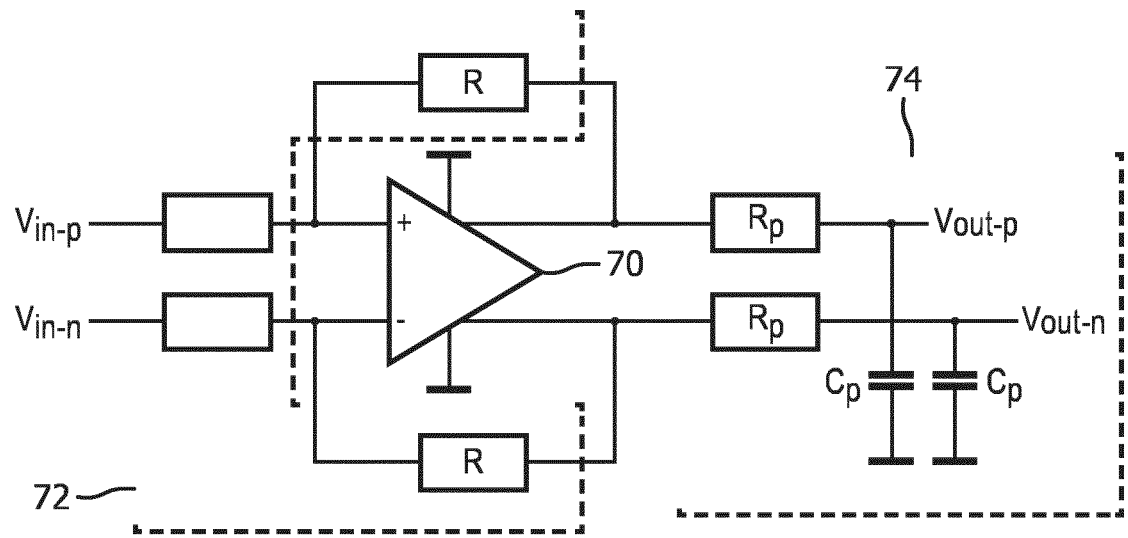
FIG. 5 shows a differential amplifier for implementing a buffer circuit.

The buffer system in FIG. 4 may be implemented using fully differential amplifiers as shown in FIG. 5. Each buffer comprises a differential amplifier 70 which is inverting with unity gain, by using an appropriate feedback resistor configuration 72. The parasitic capacitance and resistance of the lines is also shown as block 74 at the output of the amplifier 70. Each signal path comprises a series chain of the amplifier circuits of FIG. 4.

By considering the system of FIG. 5 mathematically, the output of stage n+1 is related to the output of the previous stage n by:

$$Vout_{n+1} = \frac{-Vout_n}{(1 + R_P/R)(1 + i\omega C_P R_P R/(R + R_P))}$$

Where R is the feedback resistance of the amplifier, $R_p$ is the parasitic resistance and $C_p$ is the parasitic capacitance. Then, with N stages of buffers:

$$Vout_N = \frac{(-1)^N Vout_1}{(1 + R_P/R)^N (1 + i\omega C_P R_P R/(R + R_P))^N} \approx$$

$$(-1)^N Vout_1 \left(1 - \frac{NR_P}{R}\right)\left(1 - \frac{Ni\omega\tau_{PN}}{(1 + R_P/R)}\right)$$

It can be seen that signal loss occurs in such a system even if the time constant $\tau_p = R_p C_p$ is zero. The amplifier feedback resistor R has to become very large to avoid this. The situation gets worse if $T_p$ is finite. However the time constant $T_p = R_p C_p$ decays as more buffers are added.

If the un-buffered system has a time constant $\tau_{p0} = R_{p0} C_{p0}$ the time constant with N buffers becomes $\tau_{pN} = R_{p0} C_{p0}/N^2$.

Therefore, the time constant falls faster than the number of buffers increases. Hence selecting the correct number of buffers will avoid the time constant effects, but the DC signal loss effect will still be there.

With N buffers, a buffer speed of N≥(f/f$_{po}$) is needed, so if f=40 MHz and f$_{p0}$=1 MHz then N is greater than 40.

The maximal required sample rate to perform beamforming is often quoted as 40 MHz which is denoted as f. f$_{p0}$ is ½πR$_{po}$C$_{po}$. An unbuffered system thus simply filters away the signal. Adding N=40 buffers enables the high frequencies to be seen and therefore appropriate signal sampling. The amplifiers will preferably a gain function such that their unity gain bandwidth would need to be at least 10 times higher than 40 MHz.

Figure 6:
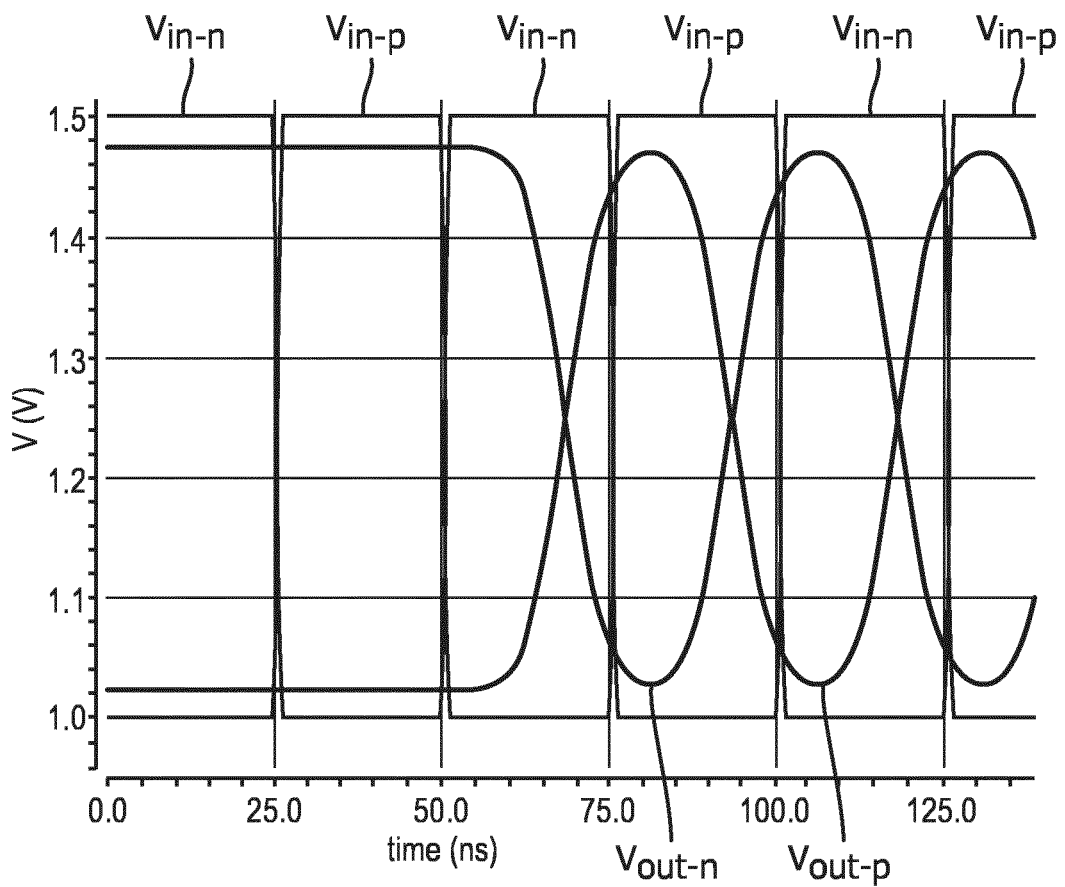
FIG. 6 shows a simulation of the system of FIG. 5.

A simulation is shown in FIG. 6 of a stepped input (complementary differential inputs V$_{in-p}$ and V$_{in-n}$) with 40 buffers having 100K Ohm feedback resistors and stage parasitic capacitance of 100 pF/40 and stage parasitic resistance of 10K/40 Ohms. At the outputs V$_{put-p}$ and V$_{out-n}$ signal loss is seen, the signal is delayed by over 50 ns. A 400 MHz amplifier bandwidth may be used with very low output impedance.

Thus, there are for example 40 buffers in series to achieve a correct sampling rate. For the example of an 800×800 transducer array, it is possible to have a maximum of 800 buffers vertically and horizontally if one buffer per transducer is used. The number of buffering operations should however be limited to reduce power consumption and also reduce noise issues. Thus, there is a compromise between reducing the time constant of the signal parasitic impedances, and reducing power consumption. The need for 40 buffering steps is simply an example to demonstrate the order to magnitude, and the 40 MHz sampling rate is again simply an example.

It will be seen that the number of buffer operations is less than the number of vertical or horizontal transducer (and hence buffer) positions (which is 800 for the example given). Thus, buffering does not take place at every buffer, but a signal path is instead defined with the desired number of buffer operations spread along the path.

The signal from each transducer may be subjected to the same number of buffering hops before the signal reaches the periphery of the array from where it is read out or converted to a digital signal. Alternatively, the number of buffering operations may depend on the position in the array, for example so that each signal path (from each individual transducer to the periphery) is formed from sections of the same unit length, which unit length defines the parasitic time constant.

Another approach is to use sample and hold circuitry.

Figure 7:
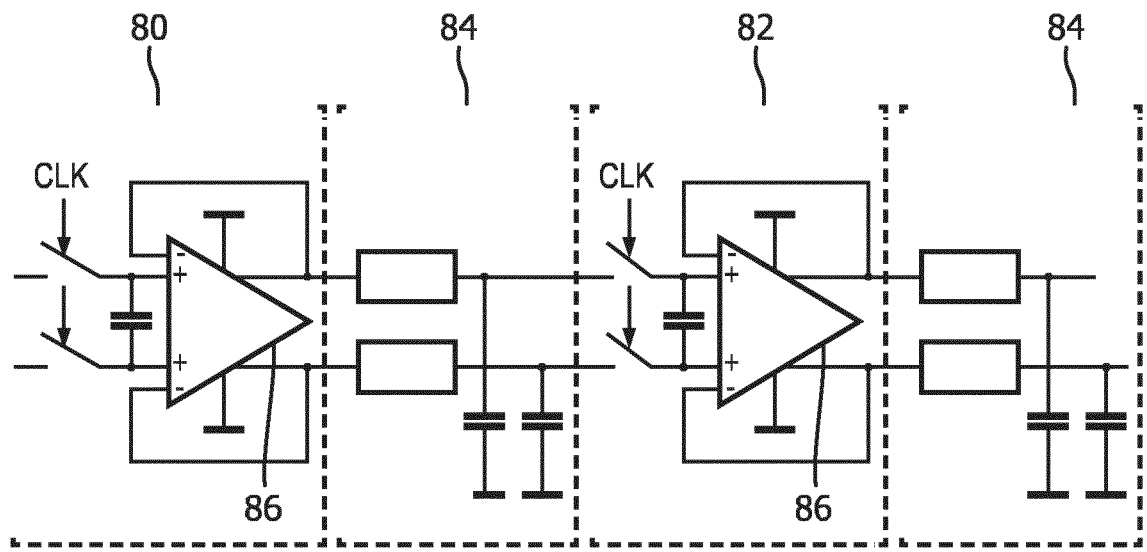
FIG. 7 shows a sample and hold circuit for implementing a buffer circuit.

FIG. 7 shows a possible solution. Two buffers 80, 82 are shown, as well as two parasitic line resistance and capacitance sections 84. Each buffer comprises a full differential buffer 86 having two differential pair input stages to enable full differential sample and hold.

By way of example, a clock running at 40 MHz samples the input which is then sampled by the next stage half a clock cycle latter (hence the complementary clocking at the input of sequential stages). The amplifiers then need far less gain bandwidth i.e. only 40 MHz rather than 400 MHz as in the example above. However the signal sees a delay of half a cycle per stage.

Figure 8:
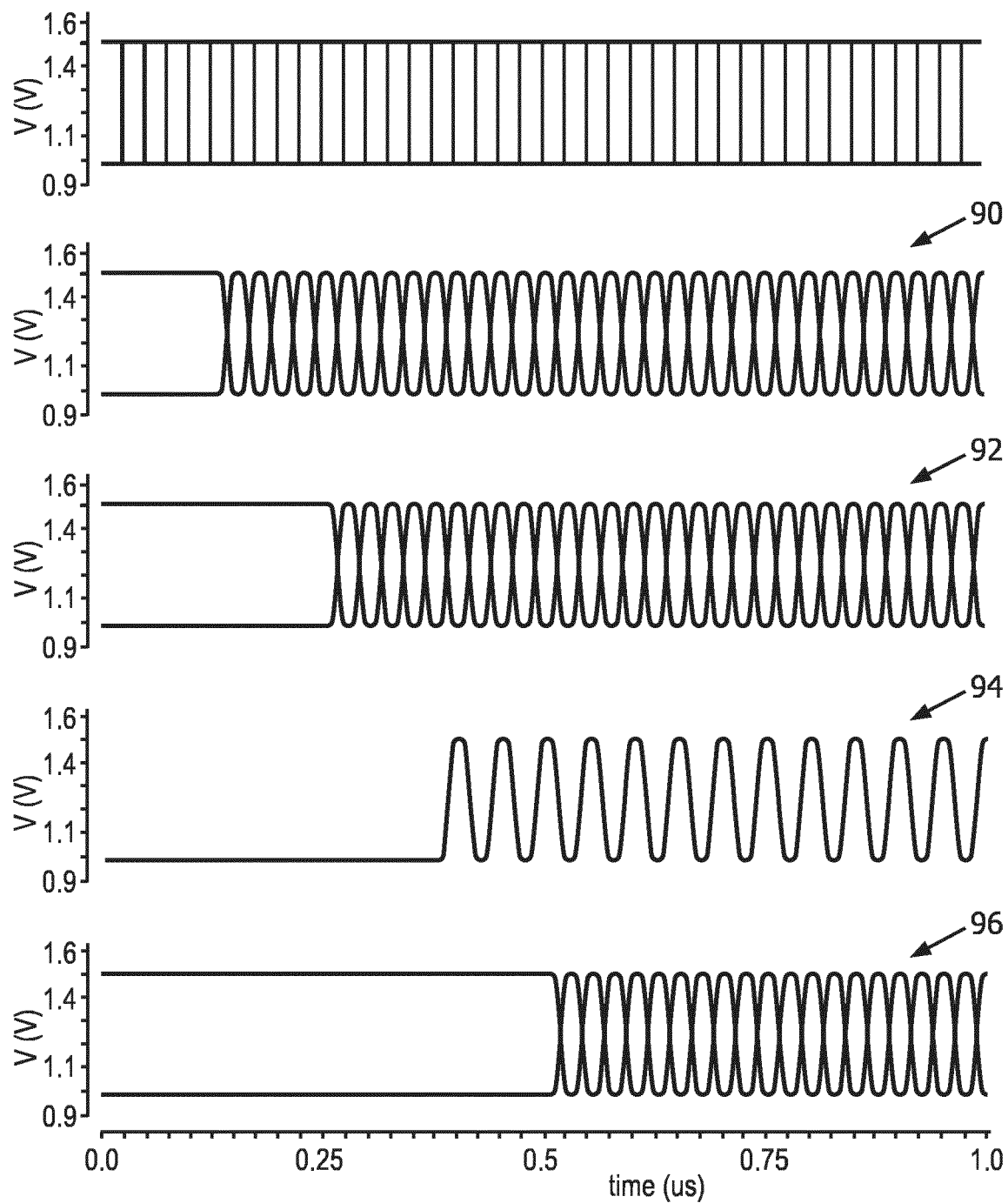
FIG. 8 shows a simulation of the system of FIG. 7.

FIG. 8 shows a simulation of this system. Outputs after 10, 20, 30 and 40 stages are shown as plots 90, 92, 94 and 96. No gain reduction is seen, so that much lower unity gain bandwidth (hence power) is used. The only issue remaining is the delay, but the size of this delay is well known.

As explained above, the aperture can be anywhere within the large array. This means that the delays can vary from zero to a maximum of perhaps 40 clock cycles. This 40 clock cycle delay can result from 40 vertical and 40 horizontal hops, each giving a half clock cycle delay. The number of hops desired again will be dictated by the sample rate. The delays need to be corrected otherwise the beamforming will be seriously compromised.

There are two possible approaches.

A first approach is to ensure that the signal paths from the array to the periphery (for example then to the analog to digital converters) is always the same length. Thus, wherever the aperture is within the larger array, the path to the converter always includes the same number of hops, i.e. the same number of sample and hold stages.

Figure 9:
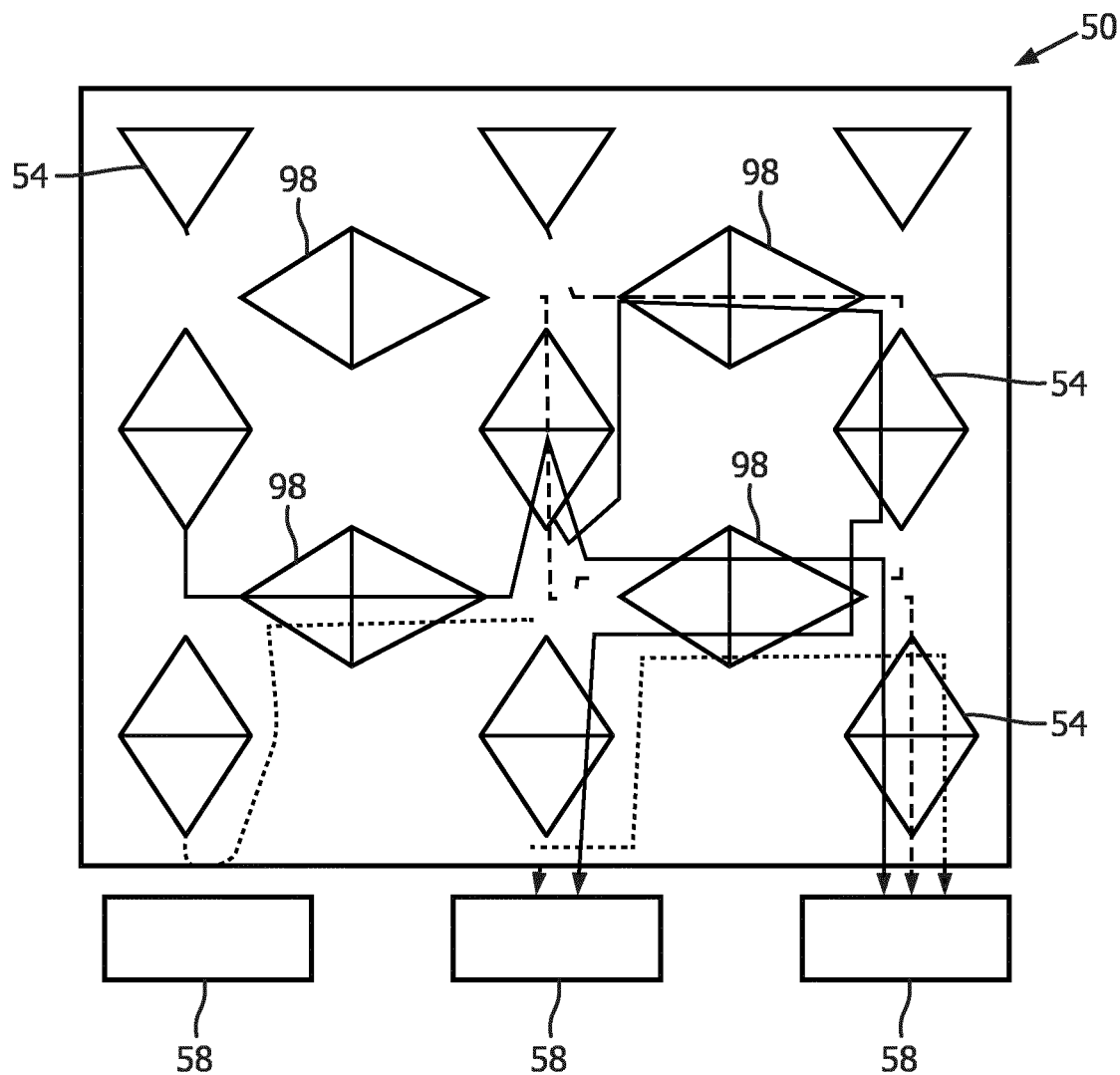
FIG. 9 shows an approach by which the signal paths from the array to the periphery are always the same length.

This approach is shown conceptually in FIG. 9 for a 3×3 example. Each transducer sub-array has a local set 54 of buffers as in the example above. In addition, a second array 98 of analog buffers is located within the area 50 of the array of ultrasound transducers, wherein the signal paths have the same number of hops for each sub-array of transducers. This is achieved by providing zig-zag paths to the periphery, and then to the banks 58 of analog to digital converters. In this simplified example, each transducer sub-array has 5 hops before reaching a bank 58 of analog to digital converters. In this way, each signal path experiences the same delay. This is of particular interest for a system using sample and hold circuits.

The final signal path locations may also be distributed along the periphery so that a distributed arrangement of analog to digital converters may be used in the same manner as explained above.

Figure 2:
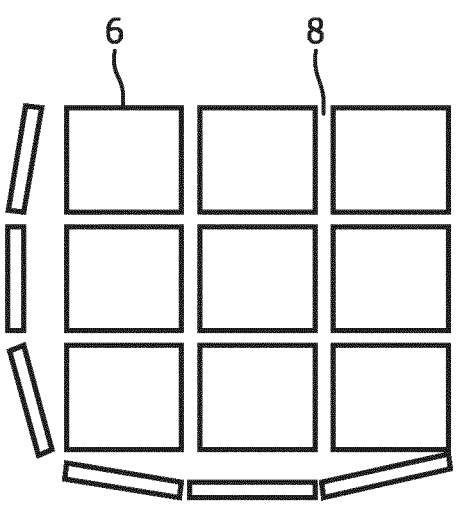
FIG. 2 shows that an array of separate probes may be provided.

Instead of equalizing the path lengths, the system may use a memory (in hardware or software) for storing information concerning a delay associated with each sub-array of transducers. A processor (e.g. 22, 26, 28 in FIG. 2) processes the transducer signals taking into account the delays stored in the memory. This processing however takes place before beamforming is applied to the data.

The number of buffering operations in this case may again depend on the position in the array.

As mentioned above, there is a local buffer associated with each transducer element of the ultrasound array. The buffer is additional to the addressing circuitry for the ultrasound transducer. Each transducer and its associated buffer may thus function either to route ultrasond transducer measurements onto an output bus, or it may perform buffering of an incident signal on an input bus and relay it to an output bus, or it may simply act in pass through mode.

Figure 10:
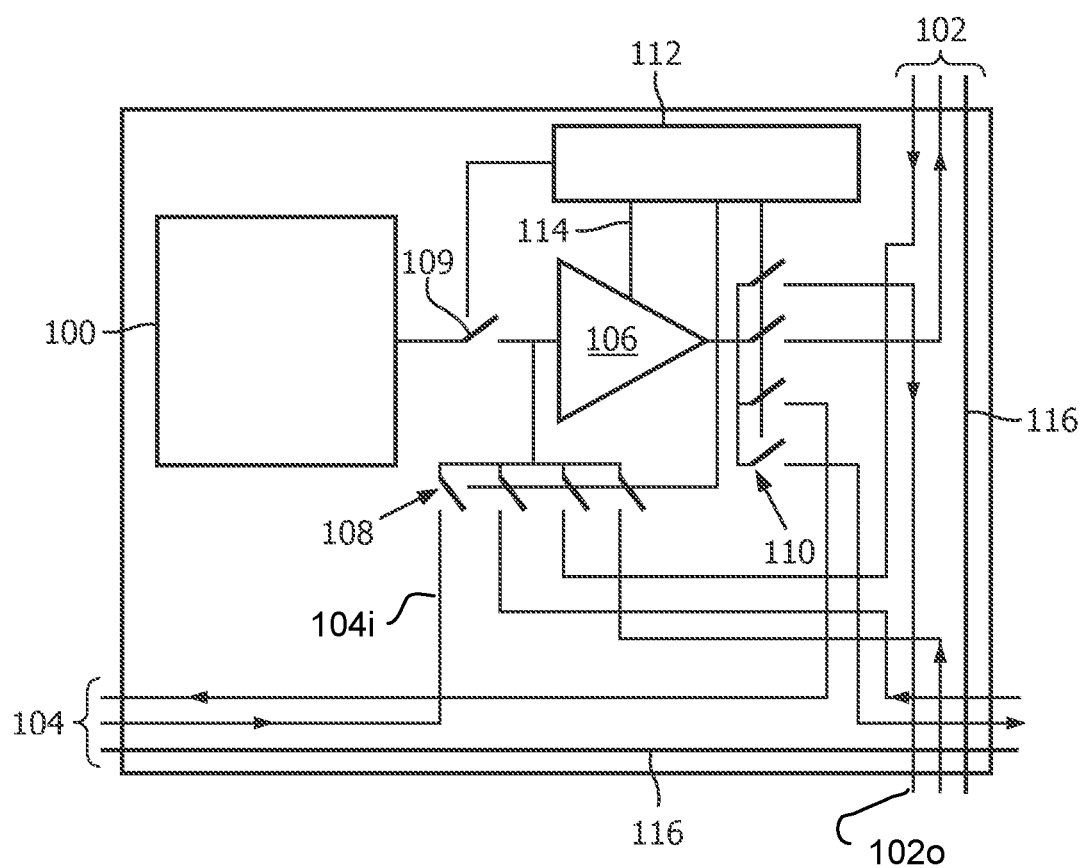
FIG. 10 shows an example of a circuit associated with one transducer element.

FIG. 10 shows an example of a circuit associated with one transducer element 100. This design enables a single array of buffers to define the zig-zag paths of FIG. 9, with each buffer being configurable to provide buffering in any desired signal path direction.

A vertical bus 102 has a width of 2 times the number of rows in the sub-array (i.e. the dynamic aperture) so that there are two lines for each transducer along the column direction. The two lines pass through the circuit and can have data passed, or added from the transducer element or buffered. The remaining lines of the vertical bus 102 may be considered to be a skip bus 116, in that those lines just skip past the transducer circuit. They are associated with transducer elements in different rows of the aperture. The width of the skip bus is thus {2×(the number of rows in the sub-array)−2} in this example.

Two lines of the bus 102 pass through the transducer circuit.

A horizontal bus 104 has a width of 2 times the number of columns in the sub-array (i.e. the dynamic aperture) so that there are two lines for each transducer along the row direction. Again, two lines of the bus 104 pass through the transducer circuit and the remaining lines may be considered to form a skip bus 116.

The circuit has a buffer 106. A first bank 108 of four switches controls the input provided to the buffer, such as shown in input 104*i*, and a second bank 110 of four switches controls where the output from the buffer, such as shown in output 102*o*, is routed.

The first bank 108 connects to:
one line of bus 104 to the left;
one line of bus 104 to the right;
one line of bus 102 above; and
one line of bus 102 below.
Similarly the second bank 110 connects to:
one line of bus 104 to the left;
one line of bus 104 to the right;
one line of bus 102 above; and
one line of bus 102 below.

This means that by activating a suitable pair of switches, one in bank 108 and one in bank 110, a signal can be received from any direction (above, below, left or right), it can then be buffered and output in any direction. Thus, the buffer function can be in line, or it can perform a right angle redirection or it can perform a U-turn.

Note that the arrangement can of course be simplified by allowing a signal path in a downward direction and a right direction. This would halve the width of each bus 102, 104.

The switches are controlled by a register 112.

The register also controls the buffer 106 itself with control line 114, and it controls switch 109 which allows the transducer element to provide its output to the buffer. Thus, the circuit may instead route the ultrasound transducer element output to a bus in any direction, with or without buffering in the circuit.

In this way, each transducer element circuit is flexible and can route data to any path, and perform buffering along any path.

The switches of the two banks can also implement a pass through mode. For example if two switches of bank 110 are closed (e.g. the top two switches) a straight through vertical path can be formed. Similarly, if two switches of bank 108 are closed (e.g. the left two switches) a straight through horizontal path is formed. Thus, the circuit may be configured in pass through mode. This pass through mode implements a cross over.

By way of example, if there are 64 row elements in one column of the aperture and there is one buffer per transducer element, then a bus of 64 wires is needed in the column and only one buffer can drive one column (ignoring the bi-directionality for this example). Therefore the buffer drives the signal for 63 row elements before it can connect to a buffer buffer again. Therefore, the skip bus is 63 lines wide.

Figures 11, 12:
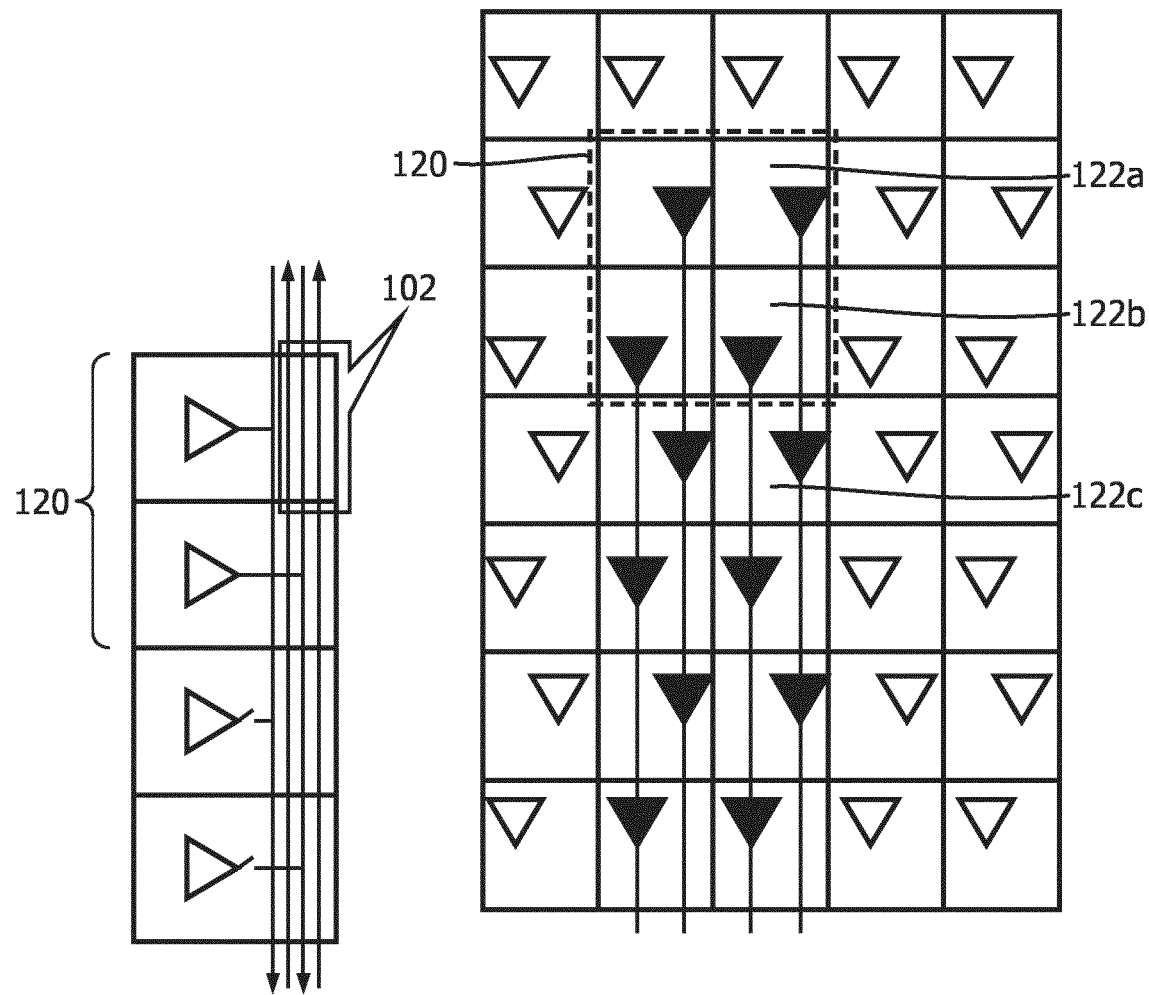
FIG. 11 shows how the skip bus in FIG. 10 connects to the transducers.
FIG. 12 shows a first example of a buffer configuration.

FIG. 11 shows how the bus 102 connects to the transducers in the aperture 120 for the simplified arrangement of the aperture having only two rows. The image shows transducers in the aperture (the top two transducers) connecting alternately to the two downward lines of the bus 102. One line is the line for that row within the aperture and the other can be considered to be the skip bus. Bidirectionality is also shown so that the bus 102 has a width equal to double the number of rows in the aperture, i.e. 4 in this simplified case so that each transducer has its own line in the skip bus heading in each direction and the other two lines may be considered to be a skip bus for that particular transducer. The connections of the transducer elements to the bus 102 then follows a checkerboard pattern.

The buffers are thus operated separately to the row and column selection of the ultrasond transducer. The selected aperture is a limited selection of elements within the total array e.g. 64×64 within 1024×1024 transducer elements. The selected aperture is slowly scanned across the array.

The register 112 is written to enable selected buffers, enable pass through of the data or output of the element data. This writing takes place dynamically during scanning of the aperture, so that the array is reconfigured for each aperture position, to provide the required combination of buffer hops. For any given aperture position, a set of buffer hops the exterior of the array can be configured.

In the example shown, the register is 10 bit. One bit is used to enable the ultrasound transducer output, one is used to enable the buffer, four are sued to route the buffer output and four are used to select the buffer input.

Although the arrangement has the flexibility to route data through any path, the data will typically be routed straight to the edge where the ADCs reside.

FIG. 12 shows a simplified example of the buffer configuration. The aperture in which the transducers are addressed is shown as region 120 comprising four transducers in order to explain the principle. The transducer signals are buffered in their initial circuits. There is then a pass through function in the next element followed by a buffering operation in the next element. For example, the transducer signals from transducer 122a are buffered initially, then pass through the transducer circuit without buffering in transducer 122b. They are then buffered in transducer element 122c. Thus, there is buffering every other transducer element.

Each transducer element may instead by a sub-array, and there is again buffering every n transducer elements, where n is the size (i.e. number of rows) of the sub-array. In pass through mode, the skip bus may be used, or else a switch configuration may provide a pass through mode.

The buffers outside the two columns are all turned off (shown as white instead of filled in). This saves power.

As the active array becomes larger, a larger number of individual transducer elements need to be skipped e.g. a 64×64 active aperture will require a skip of 63 elements, therefore the buffer drive strength needs to be sufficient to drive across the full size of an active aperture before there are available buffers for performing buffering for the next hop.

The bus lines then only connect to the transducer circuit every 64 transducers. Each line functions as part of the skip bus for the remaining 63 transducers.

Figure 13:
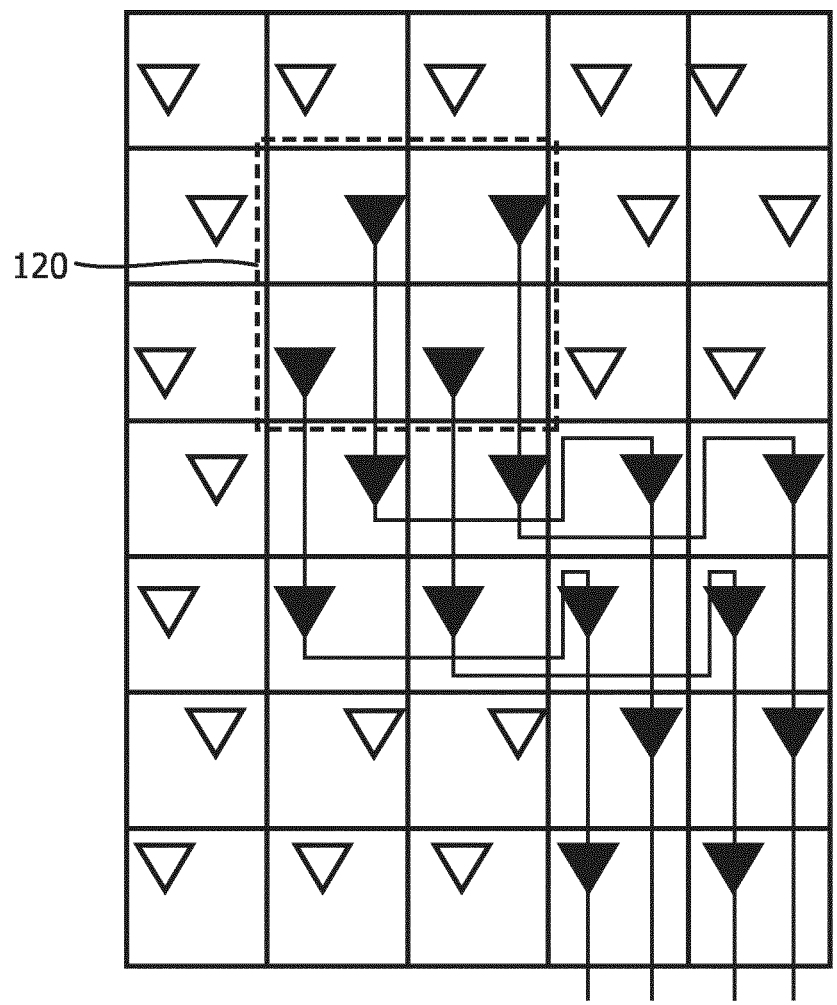
FIG. 13 shows a second example of a buffer configuration.

FIG. 13 shows an example of buffer configuration again based on a simple 2×2 aperture 120. In this example, a lateral shift is implemented across the array. Buffers not lying in the chain of signal paths can again be turned off to save power.

Figure 14:
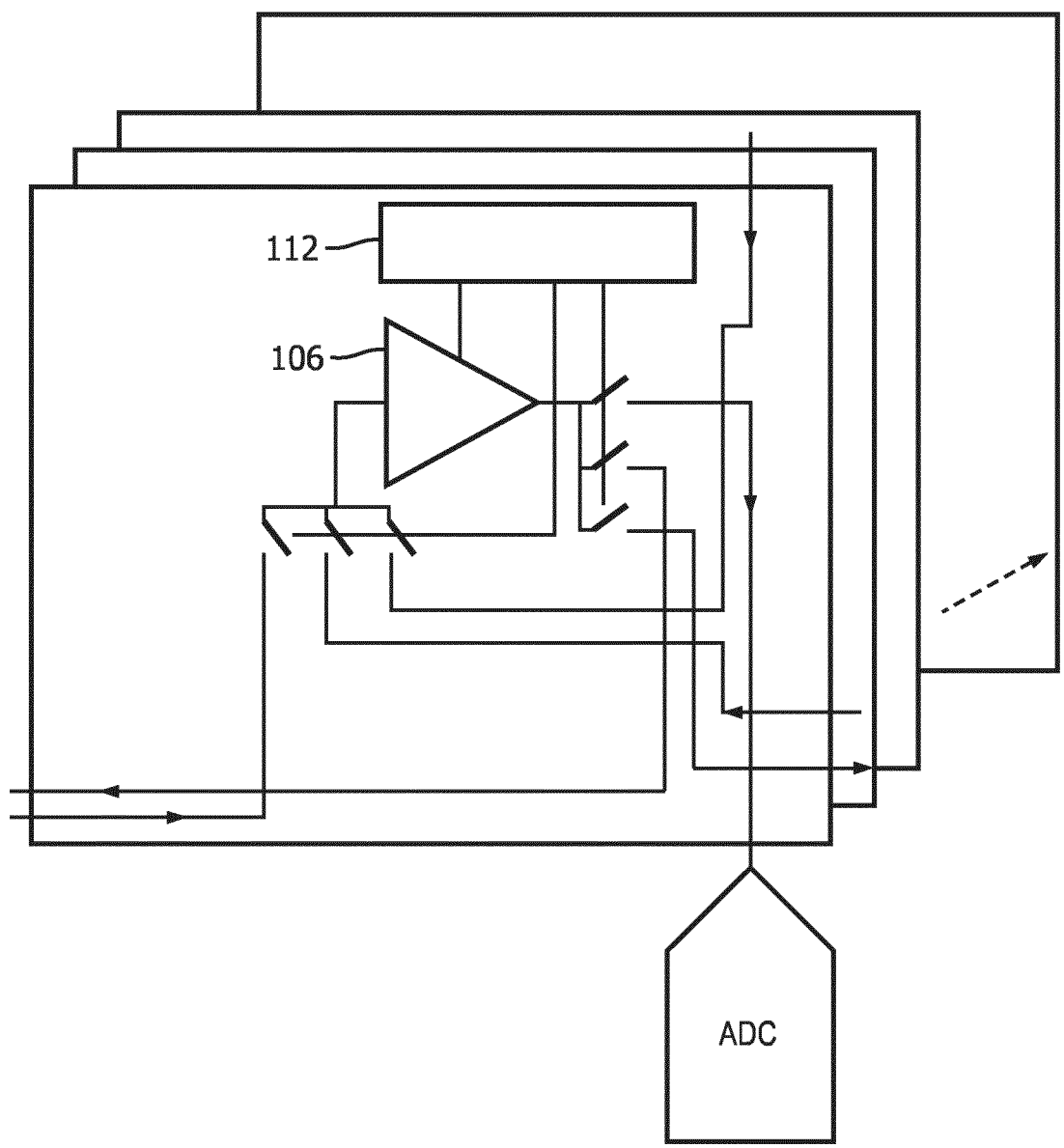
FIG. 14 shows a simplified switching arrangement for buffering in the row direction only, outside the transducer array.

FIG. 14 shows a simplified switching arrangement for buffering in the row direction only, outside the transducer array. Again, there is a buffer 106 and register 112, but there is a single column input and a pair of row bus lines. This is for routing to the ADCs which occupy the full width of the array as explained above. One such circuit is associated with each ADC, as shown.

Figure 15:
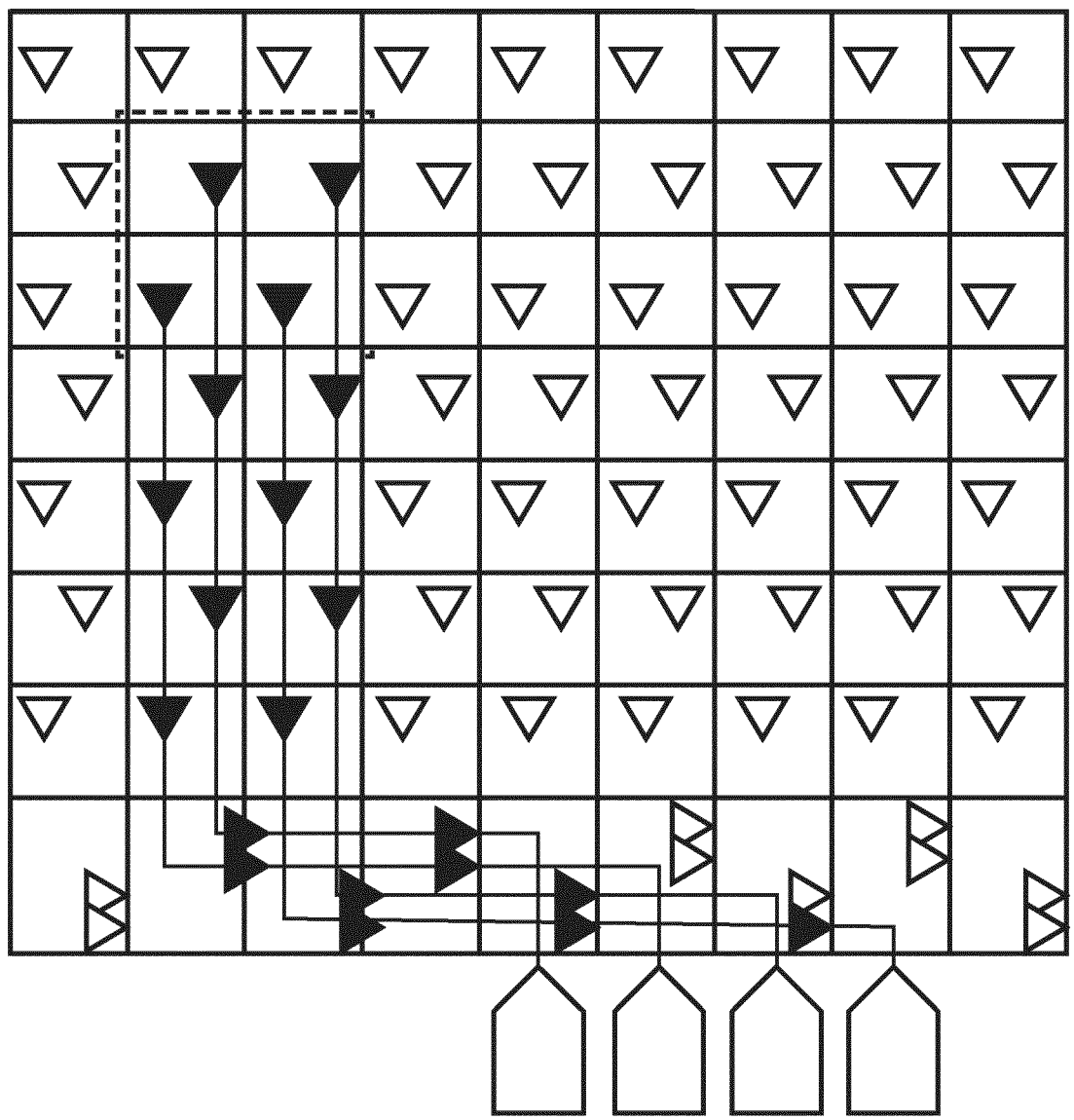
FIG. 15 shows the combination of buffering within the transducer array and horizontal buffering to the ADCs outside the array.

FIG. 15 shows the combination of buffering within the transducer array (straight down the column direction) and horizontal buffering to the ADCs outside the array.

The registers (within the array and outside the array) can be addressed to set up the relevant circuit in any manner required. The register addressing is a purely digital function that can be performed very rapidly. An on-chip controller may for example be used to perform this function which takes data from external sources to deliver the correct patterns to all of the registers.

The aperture moves slowly across the array therefore the register settings will be static most of the time.

Whilst the aperture is in one place the aperture may for example be controlled to change size from far field to near field imaging. This is a more rapid update but it does not necessarily need the register settings to change. If required, the update rate of CMOS logic should be sufficient to disable those buffers that are not required as the aperture shrinks.

The invention is of interest for large area medical ultrasound imaging.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a

The invention claimed is:

1. An ultrasound imaging system, comprising:
an ultrasound transducer array comprising a first transducer element and a different, second transducer element, wherein the first transducer element is configured to output a signal; and
a signal path for the signal output by the first transducer element from the first transducer element to outside the ultrasound transducer array,
wherein the first transducer element comprises a first circuit,
wherein the first circuit comprises:
a first analog buffer positioned local to the first transducer element;
a first external output configured to output the signal from the first circuit; and
a first switching arrangement comprising a first switch bank and a second switch bank and configured to route the signal from the first transducer element to the first external output through the first analog buffer,
wherein the second transducer element comprises a second circuit,
wherein the second circuit comprises:
a second analog buffer positioned local to the second transducer element;
an external input configured to receive the signal from the first circuit;
a second external output configured to output the signal from the second circuit; and
a second switching arrangement comprising another first switch bank and another second switch bank and configured to route the signal from the external input to the second external output through the second analog buffer,
wherein the signal path for the signal output by the first transducer element comprises the first analog buffer and the second analog buffer such that the signal is routed from the first transducer element to outside the ultrasound transducer array through the first analog buffer and the second analog buffer.

2. An ultrasound imaging method, comprising:
outputting a signal using a first transducer element of an ultrasound transducer array, wherein the first transducer element comprises a first circuit;
routing the signal output by the first transducer element on a signal path from the first transducer element to outside the ultrasound transducer array, comprising:
routing, using a first switching arrangement comprising a first switch bank and a second switch bank of the first circuit, the signal from the first transducer element to a first external output of the first circuit through a first analog buffer of the first circuit, wherein the first analog buffer is positioned local to the first transducer element;
outputting, using the first external output, the signal from the first circuit;
receiving the signal at a second circuit using an external input of the second circuit, wherein a second transducer element of the ultrasound transducer array comprises the second circuit;
routing, using a second switching arrangement comprising another first switch bank and another second switch bank of the second circuit, the signal from the external input to a second external output of the second circuit through a second analog buffer of the second circuit, wherein the second analog buffer is positioned local to the second transducer element; and
outputting, using the second external output, the signal from the second circuit, wherein the signal path for the signal output by the first transducer element comprises the first analog buffer and the second analog buffer such that the signal is routed from the first transducer element to outside the ultrasound transducer array through the first analog buffer and the second analog buffer.

3. The ultrasound imaging system as claimed in claim 1, further comprising an array of analog to digital converters and a set of signal paths including the signal path, wherein the set of signal paths leads to a bank or set of banks of the array of analog to digital converters.

4. The ultrasound imaging system as claimed in claim 1, wherein the first analog buffer and the second analog buffer each comprise a differential amplifier with unity gain or a sample and hold circuit.

5. The ultrasound imaging system as claimed in claim 1, further comprising:
a memory for storing information concerning a delay associated with the first transducer element and the second transducer element;
a processor for processing transducer signals, taking into account the delays stored in the memory.

6. The ultrasound imaging system as claimed in claim 3, wherein:
the ultrasound transducer array is provided as an integrated circuit and the array of analog to digital converters is provided as part of the integrated circuit; or
the array of analog to digital converters is provided on a separate substrate to the ultrasound transducer array.

7. The ultrasound imaging system as claimed in claim 3, further comprising an array of analog buffers, wherein the array of analog buffers comprises at least the first analog buffer and the second analog buffer, wherein the signal path comprises multiple hops between the array of analog buffers, wherein the multiple hops are spread evenly along the signal path from the first transducer element to outside the ultrasound transducer array.

8. The ultrasound imaging system as claimed in claim 3, wherein the ultrasound transducer array comprises a plurality of individual transducers elements, including the first transducer element and the second transducer element, wherein the plurality of individual transducer elements are arranged in rows and columns, and wherein the set of signal paths from within the ultrasound transducer array form columns.

9. The ultrasound imaging system as claimed in claim 8, further comprising a further array of analog buffers located in rows outside an area of the ultrasound transducer array.

10. The ultrasound imaging system as claimed in claim 8, wherein the set of signal paths have a same number of hops for each individual transducer element of the ultrasound transducer array.

11. The method as claimed in claim 2, providing, for the signal path of a set of signal paths, a connection to a respective bank or set of banks of an array of analog to digital converters.

12. The method as claimed in claim 2, wherein an array of analog buffer comprises at least the first analog buffer and the second analog buffer, wherein the signal path comprises multiple hops between the array of analog buffers, wherein the multiple hops are spread evenly along the signal path from the first transducer element to outside the ultrasound transducer array.

13. The method as claimed in claim 11,
wherein the ultrasound transducer array comprises a plurality of individual transducers elements, including the first transducer element and the second transducer element, wherein the plurality of individual transducer elements are arranged in rows and columns, and
wherein the method comprises:
   forming the set of signal paths as columns to reach an edge of an area of the ultrasound transducer array; and
   providing further signal paths between a further array of analog buffers located in rows outside the area of the ultrasound transducer array.

14. The method as claimed in claim 13, further comprising:
   forming the set of signal paths with a same number of hops for each individual transducer; or
   storing information concerning a delay associated with the first transducer element and the second transducer element in a memory and processing transducer signals, taking into account the delays stored in the memory.

15. The method as claimed in claim 11,
wherein the set of signal paths include a further array of analog buffers located within an area of the ultrasound transducer array, and
wherein the method comprises forming zig-zag signal paths within the ultrasound transducer array.

* * * * *